United States Patent [19]

Schroeder et al.

[11] 4,215,056
[45] Jul. 29, 1980

[54] FORMATION, PURIFICATION AND RECOVERY OF PHTHALIC ANHYDRIDE

[75] Inventors: Hobe Schroeder, Warrenville; David A. Palmer, Naperville, both of Ill.

[73] Assignee: Standard Oil Company (Indiana), Chicago, Ill.

[21] Appl. No.: 70,625

[22] Filed: Aug. 29, 1979

[51] Int. Cl.$^2$ ............................................. C07D 307/89
[52] U.S. Cl. ............................... 260/346.7; 260/346.4
[58] Field of Search ........................... 260/346.4, 346.7

[56] References Cited

U.S. PATENT DOCUMENTS

| 2,670,325 | 2/1954 | West et al. | 260/346.7 X |
| 3,402,184 | 9/1968 | Berthoux et al. | 260/346.4 |
| 3,484,458 | 12/1969 | Stein et al. | 260/346.4 |
| 4,165,324 | 8/1979 | Schroeder et al. | 260/346.7 |

Primary Examiner—Richard Raymond
Attorney, Agent, or Firm—Fred R. Ahlers; William T. McClain; William H. Magidson

[57] ABSTRACT

Phthalic anhydride of commercially acceptable quality is recovered in high (94–96%) yields from a mixture containing on a weight basis from 70 to 90% o-phthalic acid, 1.5 to 21% water, 0.3 up to 13% benzoic acid, 0.2 up to 2% o-toluic acid, 0.2 to 1% 2-carboxybenzaldehyde, 0.1 up to 2% phthalide and from 1.3 up to 10% higher boiling materials by rapid dehydration of o-phthalic acid to its anhydride and rapid evaporation thereof followed by contact of the resulting vapor mixture with an inert reflux liquid in a fractionation zone to remove water and to provide a partial purification of the anhydride, removal of phthalide therefrom by only heating said partially purified anhydride in the presence of a catalytic amount of an alkali metal hydroxide having a molecular weight of at least 56 followed by fractionation of the phthalide-free mixture. Such process is more commercially attractive than melting said mixture containing 70 to 90% o-phthalic acid to dehydrate it to its anhydride and recovering the anhydride by fractionation because such apparently simple process cannot produce phthalic anhydride of a color or purity to be commercially acceptable nor can it provide an anhydride product substantially free of phthalide.

6 Claims, No Drawings

FORMATION, PURIFICATION AND RECOVERY OF PHTHALIC ANHYDRIDE

TECHNICAL FIELD

This invention relates to the formation, purification and recovery of phthalic anhydride from the liquid mixture obtained by the catalytic liquid phase oxidation of o-xylene with air. More specifically according to the present invention such liquid mixture comprising on a weight basis from 70 up to 90% o-phthalic acid, from 1.5 up to 21% water, from 0.3 up to 13% benzoic acid, from 0.2 up to 2% o-toluic acid, from 0.1 up to 2% phthalide, from 0.2 up to 1.0% 2-carboxybenzaldehyde, and from 1.3 up to 10% high boiling compounds (boiling higher than 300° C.) including metal salts of organic acids (from catalyst metals) is subjected to the sequential combination of cooperating steps of dehydration under conditions evaporating phthalic anhydride, separation of water vapor from vapors of phthalic anhydride, removal of phthalide from phthalic anhydride and separation of compounds boiling above and below phthalic anhydride to recover said anhydride which as a liquid has initial and aged colors meeting the commercial specifications therefor.

RELATED PATENTS AND PATENT APPLICATIONS

U.S. patent applications Ser. No. 867,050 filed Jan. 5, 1978; Ser. No. 961,763 filed Nov. 17, 1978 and Ser. No. 50,159 filed June 20, 1979, respectively describe batchwise and modified batchwise (semi-continuous) operation, single-step continuous operation and two-step continuous operation for the catalytic neat oxidation of liquid o-xylene with air as a means for producing one type of liquid mixture feed for the present inventive combination of cooperating steps leading to purified phthalic anhydride meeting commercial specifications therefor.

Also U.S. patent applications Ser. No. 898,930 filed Feb. 1, 1979, now U.S. Pat. No. 4,165,324, is directed to the phthalide removal step of the present invention; Ser. No. 969,879 filed Dec. 15, 1978 is directed to the means for separating vapors of water and phthalic anhydride comprising a step of this invention; and Ser. No. 22,431 filed Mar. 21, 1979, now abandoned, is directed to the dehydrating of the liquid mixture containing 70 to 90 weight percent o-phthalic acid comprising a step of this invention.

All of the foregoing patent applications resulted from discoveries and developments made in our laboratories.

STATE OF THE ART

The present invention comprising a combination of cooperating steps represents a unique process for the formation, purification and recovery of phthalic anhydride from a rather impure liquid o-phthalic acid product. Since phthalic anhydride has long been produced by the air oxidation of a vapor phase of naphthalene or o-xylene in the presence of particles of a solid vanadium containing catalyst, the art pertaining to the separation of phthalic anhydride from spent air exiting such oxidation and the purification of the separated anhydride has not been found to be pertinent to the present combination of cooperating steps.

British Pat. No. 856,245 published Dec. 14, 1960 is directed to a two-step catalytic oxidation which does not use an extraneous solvent in either step and oxidizes o-xylene in the presence of cobalt or cobalt and bromine catalysis only in a mild first step, and its incomplete oxidation products are oxidized in the second step in the presence of a stronger catalyst comprising cobalt, manganese and bromine which produces a liquid impure phthalic anhydride product. Such impure liquid phthalic anhydride is refluxed with water for 90 minutes to precipitate o-phthalic acid which is recovered by filtration and the filter cake extracted with ether. The dried, ether extracted filter cake is said to be 98% pure o-phthalic acid. However the 2% impurities were not identified but probably did not contain catalyst metals. No processing scheme was presented for conversion of such 98% pure o-phthalic acid to phthalic anhydride of a commercially acceptable quality.

According to U.S. Pat. No. 3,402,184 o-xylene is oxidized with air in the presence of a liquid phase of an acetic acid solution containing cobalt, manganese and bromine ions as components of catalysis. The liquid effluent from such an oxidation contains phthalic anhydride dissolved in the acetic acid. According to the patent the liquid effluent is diluted with water and the diluted effluent is heated to its boiling point temperature to hydrolyze the anhydride to o-phthalic acid which in part precipitates from the diluted acetic acid solution. The o-phthalic acid precipitate is recovered by means for effecting solid-liquid separation (e.g., filtration). While the separated o-phthalic acid precipitate is thermally converted back to phthalic anhydride, such anhydride had only a quality of partially purified anhydride and, as such, was not of commercially acceptable quality. Also, a substantial proportion of the o-phthalic acid produced by hydrolysis of the anhydride dissolved in the liquid oxidation effluent remained dissolved in the dilute acetic acid solution. For the foregoing process to be commercially attractive such dissolved o-phthalic acid must be separated from the dilute acetic acid solution before or during recovery of acetic acid for its reuse in the o-xylene oxidation. Such second crop of o-phthalic acid or its anhydride derivative would be contaminated with catalyst metals.

With respect to the understanding and practice of the present inventive process, the fluid mixture containing mainly o-phthalic acid is produced, according to the foregoing patent applications, by the oxidation of liquid o-xylene with air or air fortified with oxygen gas to an oxygen content of up to 50 volume percent, at a temperature in the range of from 150° C. up to 250° C., in the presence of a solution of cobalt, manganese and bromine ions as components of catalysis in a solvent comprising o-phthalic acid as a major component, from 3 up to 21 weight percent water also including up to 20 weight percent acetic acid or benzoic acid to make miscible an o-xylene phase and an o-phthalic acid phase otherwise immiscible; and under a gauge pressure in the range of from 17.6 up to at least 30 kg/cm$^2$ to maintain not only a liquid phase of said solution but also to maintain equilibrium conditions favoring retention of o-phthalic acid in the free acid form rather than in the anhydride form. The cobalt component of catalysis is present in an amount based on 1 gram mole of o-xylene charged of from 0.5 up to 10 milligram atoms of cobalt. With respect to manganese, there are present from 0.05 up to 5 milligram atoms of manganese per one gram mole of xylene. Finally said catalysis has present from 0.05 up to 15 milligram atoms of bromine per one gram mole of xylene.

Semi-continuous oxidation is a modified batchwise operation comprising three operation modes wherein the middle mode of continuous xylene feed of from 80 to 95% of the xylene comes between the batchwise initiation of the air oxidation of an initial 20 to 5% of the xylene in the presence of the total amount of catalyst components to be used and the batchwise conclusion of the oxidation when only air is charged until for all practical purposes oxygen consumption has ceased.

One of said related patent applications describes a continuous single step air oxidation of o-xylene characterized by rather high conversion of o-phthalic acid such that the partially oxidized or intermediate products are of a type which, when separated, can be recycled to the o-xylene oxidation and do not inhibit, slow, or suppress the oxidation of fresh o-xylene. Another of said patent applications describes a continuous two-step oxidation operated in series flow without the need for intermediate separation attendant each step or steps as is associated with the prior art two-step oxidation process.

In the continuous neat (no extraneous reaction medium solvent) air oxidation of o-xylene, a phase miscibility problem begins to occur when the liquid reaction mixture contains about 40 weight percent o-phthalic acid. At such concentration of o-phthalic acid the o-xylene fed into the liquid reaction mixture becomes substantially insoluble therein or substantially immiscible therewith and forms a separate phase even within the stirred liquid reaction mixture. The catalyst components stay dissolved in the liquid reaction mixture and hence are not as effectively available for the oxidation of o-xylene. The oxidation continues but its vigor diminishes until the rate of oxidation becomes commercially unacceptable. Such vigor diminishing condition is readily observable from the volume ratio of o-xylene to water condensed from the exhaust from the oxidation zone. Such volume ratio is normally in the range of from 0.3:1.0 to 0.5:1.0 but the reaction's diminishing vigor is indicated by change of such ratio to 1:1 and finally to 2:1 for an unacceptable reaction rate.

However, by continuously adding either acetic acid or benzoic acid to the oxidation zone in an amount of from 5 up to 25, preferably 7 to 10, weight percent of the o-xylene, as is done in the one-step continuous oxidation, such condition of formation of two distinct substantially immiscible phases does not occur and a commercially acceptable rate of conversion of o-xylene and yield of o-phthalic acid can be obtained by the one-step continuous process.

The same problem of formation of two distinct substantially immiscible phases can be overcome simply by use of two series connected oxidation steps. The first oxidation step is conducted under mild conditions to a liquid reaction product containing less than 40 weight percent and preferably less than 25 weight percent o-phthalic acid. Ideally the extent of oxidation in the first step would be substantially complete conversion of o-xylene with the oxidation products being mainly o-toluic acid with small amounts of 2-carboxybenzylalcohol and 2-carboxybenzaldehyde and no o-phthalic acid. Then the liquid reaction mixture produced by the mild first step is oxidized in a more severe second oxidation step. The difference in severities of the first and second oxidation step can be accomplished by using low temperature in the first step and a combination of high temperature and long residence time in the second step or low temperature and catalyst concentration in the first step and high temperature, higher catalyst concentration and longer residence time in the second step.

In TABLES I and II to follow typical compositions are given for the final reaction effluents from batchwise, semi-continuous, continuous one-step, and continuous two-step operations of the above characterized neat catalytic oxidations of liquid o-xylene with air. The components are shown in weight percent of the composition.

TABLE I

| Reaction Effluent Compositions | | | | | |
|---|---|---|---|---|---|
| Components: | 1 | 2 | 3 | 4 | 5 |
| o-Phthalic Acid | 88.80 | 91.9 | 71.0 | 76.0 | 91.9 |
| o-Toluic Acid | 0.57 | 0.24 | 1.05 | 1.92 | 1.03 |
| Phthalide | 1.05 | 0.10 | 1.22 | 1.92 | 0.54 |
| 2-Carboxybenzaldehyde | 0 | 0.90 | 0.22 | 0.13 | 0.50 |
| High Boilers | 3.51 | 1.36 | 2.17 | 2.89 | 1.79 |
| Water | 5.0 | 4.9 | 20.50 | 5.75 | 3.45 |
| Benzoic Acid | 0.86 | 0.6 | 0.35 | 11.20 | 0.81 |
| Acetic Acid | 0 | 0 | 3.53 | 0 | 0 |

TABLE II

| Reaction Effluent Compositions | | | |
|---|---|---|---|
| Components: | 6 | 7 | 8 |
| o-Phthalic Acid | 86 | 84.8 | 86.9 |
| o-Toluic Acid | 0.8 | 0.78 | 0.13 |
| Phthalide | 0.08 | 0.82 | 0.07 |
| 2-Carboxybenzaldehyde | 0 | 0.52 | 0.05 |
| High Boilers | 3.02 | 7.53 | 3.4 |
| Water | 4.87 | 4.5 | 3.4 |
| Benzoic Acid | 7.6 | 1.96 | 7.84 |

STATEMENT OF THE INVENTION

The present invention comprises the formation, purification and recovery of phthalic anhydride from a liquid mixture containing on a weight basis from 70 up to 90 percent o-phthalic acid, from 1.5 up to 21 percent water, from 0.3 up to 13 percent benzoic acid, from 0.2 up to 2 percent o-toluic acid, from 0.1 up to 2 percent phthalide, from 0.2 up to 1 percent 2-carboxybenzaldehyde, and from 1.3 up to 10 percent higher boiling compounds including organo-metallic (from catalyst metals) compounds by the sequence of steps comprising dehydration of said liquid mixture under conditions which rapidly evaporate the phthalic anhydride formed by dehydrating o-phthalic acid, separation of water vapor from vapors of phthalic anhydride and compounds vaporized and entrained therewith during said dehydration-evaporation step by direct contact with a water immiscible heat exchange liquid boiling at a temperature below the boiling temperature of phthalic anhydride and at a temperature above the freezing point temperature of phthalic anhydride, removal of phthalide from phthalic anhydride by heating a mixture thereof and phthalide to a temperature of at least 200° C. in the presence of a catalytic amount of alkali metal hydroxide having a molecular weight upward from 40, and separation of commercial quality phthalic anhydride from said phthalide-free mixture by fractionating it at subatmospheric pressure in a known manner into a first fraction containing mainly benzoic acid, a phthalic anhydride product fraction and a bottoms fraction containing compounds boiling at a temperature above the boiling temperature of phthalic anhydride.

SPECIFIC EMBODIMENTS

A. Dehydration of o-Phthalic Acid to Phthalic Anhydride

The recovery of a partially purified phthalic anhydride (PAN) from the liquid effluent containing, on a weight basis, from 70% up to 90% o-phthalic acid, from 1.5 up to 21% water, from 0.3 up to 13% benzoic acid or up to 5% acetic acid and impurity amounts of oxygen containing aromatic compounds boiling above and below the boiling temperature of PAN including precursors of o-phthalic acid as well as compounds containing cobalt, manganese and bromine derived from the catalysis used for the preparation of such effluent, is characterized by the continuous in situ dehydration of o-phthalic acid to PAN and flash evaporation of it from the liquid effluent leaving a fluid residue containing the materials boiling above the boiling temperature of PAN, continuously removing the vapor fraction and the liquid residue fraction as separate streams from the site of such dehydration and flash evaporation.

Such rapid dehydration to and evaporation of partially purified PAN can be suitably effected by introducing the fluid oxidation product into a combination dehydration-evaporation zone maintained at a pressure in the range of from 760 mm down to 40 mm Hg, preferably in the range of from 250 mm down to 75 mm Hg, and at a temperature in the range of from 180° C. up to 250° C. and removing from such zone the separate vapor fraction stream and the liquid residue stream.

For efficient fluid flow out of the dehydration-evaporation zone the fluid residue, i.e., a mixture containing materials boiling at a temperature above the boiling temperature of PAN, can contain from 10 up to 60 weight percent PAN as a viscosity reducing flux. Loss of PAN to the residue will be from one up to four weight percent of the PAN equivalent of o-phthalic acid in the feed. Much of the residue's PAN can be extracted by water as o-phthalic acid.

The mixture of vapors withdrawn from the heating-vaporizing zone comprises water as the non-organic portion and the organic portion comprising mainly (81–99 wt%) PAN together with benzoic acid (up to 13 wt%) and/or acetic acid (up to 5 wt%); the precursors (o-toluic acid, 2-carboxybenzaldehyde and phthalide) which amount in toto to from 1.13% up to 1.8% by weight; and the accompanying bromine-containing compounds in amounts of less than 1000 ppm.

Removing the fraction comprising the mixture of vapors and the fluid metals-containing bottoms fraction from the heating and vaporizing zone substantially as rapidly as such fractions are formed minimizes contact between liquid PAN and the metals containing bottoms fraction. Such minimum contact is an essential critical feature of the present invention. We have found that moderate to relatively long contact between liquid PAN and said metals-containing residue fraction enhances decomposition of PAN thereby lowering its yield and adds, in some way, new colored or color-forming impurities which cannot be removed from PAN by any commercially feasible and economic process.

The liquid effluents from the various neat oxidations of liquid o-xylene are obtained therefrom at a temperature of from 150° C. up to 250° C. and a pressure of from 17.6 kg/cm² up to 30 kg/cm². Since the foregoing step is conducted at a lower pressure of from one atmosphere (760 mm Hg) down to 0.05 atmosphere (40 mm Hg), sudden decompression of said liquid effluent to such lower pressure could cause solidification of the effluent unless it is maintained at a temperature at which the effluent remains a liquid. This can be readily accomplished by combining the effluent with additional liquid water at the effluent's pressure to increase the water content to 15 to 20 weight percent of the diluted effluent and maintaining its temperature at 200° C. to 220° C. and feeding such diluted effluent into the dehydration and evaporation zone. Alternatively, the liquid effluent can be used directly by combining it with a large volume of rapidly circulating liquid residue (PAN and water-depleted effluent).

B. Separation of PAN from Mixture of PAN and Water Vapors

The separation of phthalic anhydride from a vapor mixture containing 60 to 85 weight percent of said anhydride and 25 to 10 weight percent water vapor with the remainder comprising vapors of benzoic acid, o-toluic acid and materials boiling near or just above said anhydride withdrawn from the previous step involves contacting such vapor mixture in countercurrent flow with a reflux liquid at a temperature below the boiling point of phthalic anhydride to condense it and dissolve its condensate. Said separation is effected by exchange of heat from the vapor mixture to vaporize some of the reflux liquid. Its vapors and water vapor move upward in a rectification zone countercurrent to the flow of reflux liquid and form a vapor mixture enriched in water vapor and vapor of the reflux liquid but depleted in vapors of benzoic acid, toluic acid and aromatic compounds having boiling temperatures above that of water but below such acids. Such enrichment in water vapor and vapors of reflux liquid continues until the rising vapor mixture contains substantially only vapors of water and the reflux liquid. The mixture of substantially only vapors of water and reflux liquid is cooled to a temperature below the boiling temperature of water, thereby condensing both the reflux liquid and water. The water condensate separates from the reflux liquid's condensate. The water layer is discarded. The cool reflux liquid condensate layer is recycled to said rectification separation.

The reflux liquid moves from the rectification down through said contact with the feed vapor mixture to a stripping zone wherein the reflux liquid carrying phthalic anhydride condensate as dissolved liquid and/or solvent becomes enriched with respect thereto and with respect to benzoic and o-toluic acids and phthalide. The reflux liquid containing phthalic anhydride, benzoic acid, o-toluic acid and phthalide is heated to a temperature which vaporizes the reflux liquid but not phthalic anhydride but rather the heating leaves the anhydride as a liquid in which phthalide, benzoic acid and o-toluic acid become dissolved.

Such a concept for PAN separation requires as the reflux liquid a substantially pure single compound or a mixture of boiling point related compounds so that there is no component of the reflux liquid which will remain with and contaminate phthalic anhydride. The reflux liquid must be an inert solvent or absorbent for phthalic anhydride, benzoic acid, and o-toluic acid at low temperatures, e.g. below the anhydride's freezing point and up to its melting point, and miscible with said benzene carboxylic acids at higher temperatures between their melting and boiling point temperatures. The reflux liquid must be immiscible and unreactive with water to facilitate their separation for recycle of the reflux liquid and minimize its loss in the separated water condensate. The reflux liquid must have a vapor pressure higher than the vapor pressure of phthalic anhydride to be readily separable therefrom but sufficiently low to remain substantially liquid after contact with the hot, 180° to 235° C. feed, and move through the stripping zone. Lastly, the reflux liquid should not form an azeotrope with either one or all of phthalic anhydride, benzoic acid or o-toluic acid.

The most convenient use of such reflux liquid is in a combination of a rectification zone above a feed zone, a stripping zone below the feed zone, a zone for vaporizing the reflux liquid at a temperature above the melting point but below the boiling point temperatures of phthalic anhydride and transferring the reflux liquid vapors to contact the reflux liquid carrying in solution or by absorption phthalic anhydride, benzoic acid and o-toluic acid, and a zone to receive and cool the mixture of water and reflux liquid vapors to condense them for their separation and recycle of the reflux liquid condensate. Said combination of condensation zone, rectification zone, feed zone, stripping zone and reboiling zone define, of course, a fractionation system (e.g., fractionation tower or towers).

Methylbenzoate is the preferred refluxed liquid to use in the fractionation system for effectively removing water vapor from a mixture thereof with vapors of phthalic anhydride, benzoic acid, o-toluic acid and phthalide. Pseudocumene (1,2,4-trimethylbenzene) can also be used as such reflux liquid.

The amount of methylbenzoate reflux used relative to the amount of water present in the feed can vary from 8 to 20 on a volume to volume basis. Typically from 0.7 up to 0.9 mole of methylbenzoate is refluxed per mole of vapor fed to the fractionating system. The amount of pseudocumene reflux liquid used is from 1.5 to 3.0 moles per mole of vapor fed to the fractionation system.

One example of such fractionation system is provided by a top recycle tray, a 15 tray column for rectification zone below the recycle tray, a feed tray below the rectification zone, and a 20 tray column as the stripping zone below the feed tray. Such trays have at least 50% separation efficiency. Both of said columns are vacuum jacketed as are the feed and recycle trays. An externally heated reboiler having a side outlet for liquid removal supplies heat for the stripping zone by vaporizing at least the reflux liquid flowing down the stripping zone into said reboiler. The reboiler is operated at a temperature of from 200° C. up to 250° C. and a pressure of from 0.19 up to 0.33 atmospheres; i.e., 150 mm Hg up to 250 mm Hg.

As it will be appreciated by a chemical process design engineer, such fractionation system towers or columns can be any of the trayed or packed columns generally useful for fractionation.

Vapor from above the recycle tray is transferred through a heat traced line to a condenser cooled to a temperature of from 25° C. up to 43° C. above a decanter from the side of which the top aqueous phase flows into a receiver and from the bottom of which the reflux liquid condensate returns through a reflux control valve and meter. A water cooled knockback condenser is in the vacuum line to minimize removal of low boiling compounds into the vacuum system. Pressure at the top of the rectification column can be maintained at 150 torr (0.2 atmosphere) by a control valve operated by a pneumatic controller and an absolute pressure transmitter.

C. Removal of Phthalide from PAN

The liquid mixture containing mainly phthalic anhydride (PAN) and impurity concentrations of benzoic acid, phthalide, o-toluic acid and 2-carboxybenzaldehyde, if any of the latter be present, is removed from the reboiler of the preceding step at 200° C. to 250° C., is held at that temperature or even heated under pressure up to 350° C. in the presence of a catalytic amount, from 1.0 up to 10 milligram moles per one gram mole of impure phthalic anhydride, of an alkali metal hydroxide having a molecular weight of at least 40 (e.g., molecular weight of 40, 56, 102 or 150). No distillation or solid-liquid separation is used in the this step of phthalide removal. Rather only the foregoing heating in the presence of said alkali metal hydroxide causes the phthalide per se to disappear (i.e., no longer analytically detectable) from the impure PAN.

The duration of such heating of impure PAN in the presence of said alkali metal hydroxide varies with the concentration of the anhydride used and with the temperature of such heating. At equal concentrations and heating temperatures the relative activities of the hydroxides are of the order of: Na<K<Rb<Cs. The phthalide removal activities of the different alkali metal hydroxides can be illustrated by their use at 275° C. for four hours at the concentration of 3.7 milligram mole per one gram mole of impure PAN containing 0.78 weight percent phthalide. After such treatment the samples of PAN were found by analysis to contain the residual concentrations of phthalide shown in TABLE III to follow.

TABLE III

| Hydroxide | Residual Phthalide, wt. % |
|---|---|
| LiOH | 0.37 |
| NaOH | 0.21 |
| KOH | 0.008 |
| RbOH | 0.007 |
| CsOH | <0.001* |

*Limit of detectability is 10 ppm (0.001%) by weight.

Based on activity for phthalide removal as indicated in TABLE III the preferred alkali metal hydroxides are those having a molecular weight of 56, 102, and 150; i.e., the hydroxides of potassium, rubidium and cesium. Based on economics the use of potassium hydroxide is preferred because on a unit weight basis the hydroxides of rubidium and cesium costs are several hundred times that of potassium hydroxide. Therefore the most preferred alkali metal hydroxide is potassium hydroxide.

The variance of activity with temperature of the alkali metal hydroxides in this step can be illustrated by the use of 3.7 milligram moles per one gram mole of impure PAN and determining the half period (time for phthalide concentration to diminish by one-half) at different temperatures. Such half periods for said concentration of KOH are 10 minutes at 275° C., 103 minutes at 250° C. and (by extrapolation) more than ten days at 200° C.

The normal (760 mm Hg) boiling temperature of the impure PAN is about 275° C. Thus this step on the basis of operating time can be carried out suitably at a temperature from 250° C. up to 350° C. and preferably at a temperature of from 275° C. up to 300° C. Hence the operating pressure is rather moderate and can be from one atmosphere (0 kg/cm² gauge pressure) with added inert gas up to 1.45 atmosphere (0.5 kg/cm² gauge pressure) at 300° C. with no added inert gas.

Impure PAN having a phthalide content of up to 2.0 weight percent can, upon treatment at 257° C. for four hours with 3.7 milligram moles KOH per one gram mole of impure PAN, decrease in phthalide content to less than 0.001 weight percent.

D. PAN Recovery by Fractionation

Following the foregoing step of phthalide removal, the hot impure PAN is charged directly to a fractionation step conducted in known manner. Such fractionation of impure PAN containing benzoic acid, o-toluic acid and 2-carboxybenzaldehyde can be conducted at an operating pressure in the range of from 20 mm Hg up to 760 mm Hg absolute (i.e., from 0.026 up to 1.0 atmospheres). For continuous operation the fractionation is conducted in two series connected towers. The benzoic acid fraction is removed as the top fraction of the first tower and the PAN Product is removed as the top fraction of the second tower. Operating at such pressures, the impurities, mainly benzoic and o-toluic acids, can be readily removed at reflux ratios of from 10:1.0 up to 50:1.0 as a first or light end fraction amounting to about one percent by weight more than the sum of the impurities content. For example, when the phthalide-free impure PAN has a total impurity content of 2.6 weight percent, the first fraction taken will amount to 3.6 weight percent of the impure PAN charged. The reflux ratio will depend on the size of the light end (benzoic acid-containing) impurity fraction relative to the feed. Minimum reflux ratio requirements are fixed by vapor-liquid equilibrium compositions and acceptable losses of PAN. As the reflux ratio is descreased, as evident to one skilled in the art, the PAN loss to the light end fraction will increase.

The PAN product fraction can then be taken at a reflux ratio of from 1:1 to 5:1, preferably 1:1 to 2.5:1. There is left a residue (bottoms fraction of the second tower) containing reaction products of the alkali metal hydroxide and condensation products whose formation (e.g., product of the reaction of phthalide with PAN and/or benzoic or o-toluic acid) are catalyzed by the hydroxide. Such bottoms or residue fraction will amount to about 1 to 5 weight percent of the PAN charged and will contain 25 to 50% PAN so that the residue as a liquid has a viscosity such that it does not present a fluid transfer (gravity flow or forced flow) problem. The use of a viscosity lowering addition agent can decrease said loss of PAN to the bottoms fraction.

The examples to follow are provided to enable those skilled in the art to understand and practice the present invention.

EXAMPLE 1

For the o-phthalic acid dehydration to PAN and its flash evaporation in this example the dehydration-evaporation vessel used is a thin film dehydrator-evaporator having an evaporation surface of 2546 cm². Said evaporation surface is the surface of a horizontal cylinder rotatable in a tapered jacketed chamber. Said cylinder has on its surface four blades which have a 1.0 mm clearance from the inner jacket surface. The cylinder rotates at 1800 rpm for a tip speed of 10 m/sec. The vapor-liquid disengagement section is heated electrically to 180° C. The jacket is heated with circulating oil preheated to a temperature of 220° C. The jacket is co-extensive with the rotatable cylinder. A flanged glass residue receiver is located in the bottom of the vapor-liquid disengagement zone. A removable tubular vapor outlet containing a glass wool demister pad is connected to the feed inlet of a fractionation unit in which the reflux liquid is methylbenzoate.

An adjustable ram valve feeder is in the dehydrator-evaporator end of the fluid transfer line between the oxidation vessel wherein the catalytic neat oxidation of liquid o-xylene with air occurs at a gauge pressure of 28 kg/cm². Near the oxidation vessel end of the fluid transfer line there is a check valve to prevent back flow from the transfer line to the oxidation vessel. Between said check valve and said ram valve feeder there is an inlet in the transfer line to receive water under pressure.

Step (a) Dehydration-Evaporation

The feed for the thin film evaporator comprises liquid oxidation effluent diluted with water to 18.5 weight percent and maintained under a gauge pressure of 10.2 kg/cm² and a temperature of 200° C. Said feed is introduced at a rate of 31.2 grams per minute into the thin film evaporator operated at a subatmospheric pressure of 210 to 230 mm Hg (0.276 to 0.30 atmosphere), at a feed section temperature of 230° C. and a liquid-vapor disengagement section temperature of 210° C. The residual liquid collected from the evaporator amounts to about 3.3 weight percent of the oxidation effluent fed to the evaporator. Said residue contains on a weight basis 55.6% PAN, 0.99% benzoic acid, 0.18% o-toluic acid, 0.068% 2-carboxybenzaldehyde, 0.58% phthalide, and 43.6% higher boiling compounds including organometallic compounds from the metal catalyst components. The feed and vapor mixture compositions are, on a weight basis, shown in TABLE IV to follow.

TABLE IV

| COMPOSITION OF FEED TO AND VAPOR FROM EVAPORATOR | | |
|---|---|---|
| Component, wt. % | Feed | Vapor |
| o-Phthalic Acid (Phthalic Anhydride) | 65.5 | 60.2 |
| o-Toluic Acid | 1.49 | 1.58 |
| 2-Carboxybenzaldehyde | 0.02 | 0.02 |
| Phthalide | 0.22 | 0.22 |
| Benzoic Acid | 10.3 | 10.9 |
| High Boiling Compounds* | 4.2 | 0 |
| Water | 18.5 | 27.1 |

*"High Boiling Compounds" include metal salts of organic acids.

The above vapor composition comprises 94.4% of the feed to the evaporator or 29.46 grams per minute of vapor mixture and contains 0.8 weight percent organic bromides.

Step (b) Separation of Water Vapor from PAN

Said vapor mixture is fed to a fractionating column of the type before described but of larger volume and for separation of water vapor from PAN by the use of methylbenzoate as reflux liquid. The volumetric reflux ratio of methylbenzoate to water is 20:1.0. The column is operated at a subatmospheric pressure of 150 mm Hg (0.197 atmosphere) and a reboiler temperature of 215° C. The liquid product drawn from the reboiler (20.2 grams per minute) contains on a weight basis 85.9% PAN, 2.23% o-toluic acid, 0.03% 2-carboxybenzaldehyde, 0.32% phthalide, 11.1% benzoic acid and has a bromine (organic bromide) content of 0.5%.

Step (c) Removal of Phthalide

The liquid withdrawn from the foregoing step (b) is combined with 7.4 milligram moles of KOH per 1.0 gram mole of PAN and the mixture heated to a temperature of 275° C. for four hours. At the end of such heating the phthalide content of the liquid will be found by analysis to be less than 0.001 weight percent.

Step (d) Fractionation

The liquid from step (c) is charged to fractionation equipment, whose two towers have trays of 50% separation efficiency, operated at 0.13 atmosphere. A first (top) fraction is taken from the first tower at a reflux ratio of 50:1 in an amount of 14.5 weight percent of the liquid charge. Said first fraction contains all the benzoic acid, o-toluic acid and 2-carboxybenzaldehyde but only a small amount, 1.27%, of the PAN content of the materials charged to fractionation. The bottoms from the first tower flows as feed to the second tower where the PAN product fraction is taken at a reflux ratio of 2.5:1. Said product PAN fraction amounts to 97.8% of PAN content of the materials charged to the first tower in this fractionation step. The bottoms fraction comprises about one percent of the materials charged to the fractionation and contains about 50 weight percent PAN.

The product PAN fraction as a liquid will have an initial APHA color of 10 (Pt-Co scale) and an aged (ASTM TEST Method D1209-69) APHA color of 40. The purity of the PAN product recovered from the foregoing process will be at least 99.8%.

The foregoing example of the present invention illustrated the dehydration-evaporation step by the use of liquid oxidation effluent water diluted and maintained at a temperature of 200° C. and a gauge pressure of about 10 kg/cm$^2$ fed to the thin film dehydrator-evaporator operated at a subatmospheric pressure of from 0.276 to 0.3 atmosphere and a temperature of from 210° C. up to 230° C. with intermittent feed thereto. For continuous feed of the liquid effluent of neat o-xylene oxidation which can be at a temperature as high as 240° C. and a gauge pressure of 30 kg/cm$^2$ there is suitably at least one step of decompression to a gauge pressure in the range of from 5 to 12 kg/cm$^2$ when the liquid feed enters the dehydration-evaporation operation at a subatmospheric pressure of 40 to 250 mm Hg. Such decompression can be conducted through a pressure reducer which discharges the decompressed liquid below the surface of the liquid contents in a surge drum. Or the step of decompression can be accomplished by a means analogous to the ram valve feeder used in the foregoing example. Such decompression is useful to avoid the sudden formation of solids and likely attendant plugging of the fluid transfer apparatus elements during decompression of the feed from the gauge pressures of 25 to 30 kg/cm$^2$ down to 40 to 200 mm Hg. Partial decompression for such purpose can be accompanied by water dilution of the liquid oxidation effluent when it contains less than 15 weight percent; e.g. from 3 to 15 weight percent, water. Such dilution can be done by the addition of steam condensate to the liquid effluent before its decompression to also avoid solidification of the decompressed feed. Dilution for such purposes can be to a water content up to 25, preferably a water content of 17 to 25 weight percent. Such amounts of water in the feed which evaporates with PAN acts to sweep it from the dehydration-evaporation step.

Another mode of practice of the dehydration-evaporation step of the present invention comprises the following procedural steps conducted in the manner and under the conditions described which involve a different concept for decompressing the oxidation reaction effluent.

The flow system used in the following illustrative example has been specially devised to compress the fluid reaction effluent from the neat catalytic oxidation of liquid o-xylene with air. It will be appreciated that decompression of such fluid effluents from a gauge pressure of from 17 up to 28 kg/cm$^2$ (absolute pressure of from 18 up to 29 kg/cm$^2$) down to a pressure of from 760 to to 40 mm Hg (absolute pressure of from 1.03 down to 0.054 kg/cm$^2$), preferably 250 down to 100 mm Hg, would be accompanied by instantaneous evaporation and resultant precipitation of solids. Such instantaneous precipitation of solids would plug the inlet to the combination dehydration-evaporation zone because there is not sufficient liquid held therein to effectively prevent such solids precipitation upon injection of the fluid effluent below the liquid in said zone. The concept applied in solving said problem associated with the substantial decompression of the fluid effluent feed is to absorb the pressure drop energy by momentum transfer to a circulating liquid.

It will also be appreciated that the heat necessary to dehydrate o-phthalic acid in the oxidation effluent and evaporate its anhydride is not available in the fluid effluent going to the dehydration-evaporation zone. Hence additional heat must be supplied to said zone but must be done in such a manner so that the residence time in said zone and such heat addition do not cause decomposition and added discoloration of the phthalic acid anhydride product. By only dehydrating about 97 to 98% of the o-phthalic acid (PA) to its anhydride (PAN) in said combination zone there is left a rather small amount of fluid containing catalyst component. Such fluid can be rapidly circulated from said combination zone through an indirect heat exchange zone which provides the additional heat and then back into the combination zone. Such circulation for heat addition and retention of a small amount of fluid in a sump to supply such circulation can be accomplished in a total residence time of from 1.0 up to 2.0 minutes, an adequately short residence time to avoid the decomposition and added discoloration.

The foregoing concept of absorption of pressure drop energy by momentum transfer can be practiced by injecting the pressurized fluid reaction effluent into the fluid circulating from the combination zone through an external heat exchange zone back to the combination zone.

EXAMPLE 2

(a) Dehydration-Evaporation

In this example 1231.9 kg/hr of fluid oxidation effluent ("F.O.E.") produced by the continuous catalytic neat oxidation of liquid o-xylene is decompressed from 26.72 kg/cm$^2$ absolute pressure and a temperature of 214° C. by injecting such effluent into 13444.7 kg/hr of circulating ("cycle") fluid which is most (about 99%) of the concentrate produced in the combination dehydration-evaporation zone. The smaller part (0.9 to 1.0%) of the concentrate, here 122.6 kg/hr, is withdrawn and mixed with 7.3 kg/hr of steam at a temperature of 160° C. and an absolute pressure of 5.98 kg/cm$^2$. Such mixture is fed to a stirred film evaporation zone operated at a temperature of 227° C. and an absolute pressure of 0.246 kg/cm². From the stirred film evaporation zone there are withdrawn 56.9 kg/hr of residue and 73 kg/hr of vapor mixture containing 95.3% phthalic acid anhydride (PAN). Said vapor mixture is fed into the vapor space above the combination dehydration-evaporation zone.

By injecting the 1231.9 kg/hr of fluid oxidation effluent at a temperature of 214° C. and an absolute pressure of 26.72 kg/cm² into the 13444.7 kg/cm² circulating ("cycle") liquid at a temperature of 202° C. and an absolute pressure of 0.246 kg/cm² there is produced a composite feed ("Feed") for the combination dehydration-evaporation zone amounting to 14676.6 kg/hr at a temperature of 199° C. and an absolute pressure of 0.492 kg/cm². Said feed is heated by indirect heat exchange to a temperature of 218° C. and thereafter flows into the combination zone operated at an absolute pressure of 0.246 kg/cm². Such operation of the combination zone results in the production of 1109.3 kg/hr of a mixture of vapors and gases containing 77.6 weight percent PAN. Such mixed vapors are combined with the vapors drawn from the wiped film evaporator. The combined mixtures of vapors and gases comprise the "Crude PAN Product" to be fed to the subsequent step of separation of PAN from water vapor according to the present illustration of this invention.

The amount (13444.7 kg/hr) of "cycle" liquid might appear to violate the previous caution with respect to long residence exposure to dehydration-evaporation conditions. However, the low volume of such "cycle" liquid held in the combination zone and the high recycle rate of such "cycle" liquid result under the foregoing conditions of a rather low, 1.3 minutes, residence time in said zone as well as in the reheating (indirect heat exchange) zone.

The compositions of the foregoing streams of fluids and mixtures of vapors are shown in TABLE V to follow.

TABLE V

| FLUID STREAMS COMPONENTS, WEIGHT PERCENT | | | |
|---|---|---|---|
| | Dehydration-Evaporation Zone | | |
| Component | "F.O.E." | "Cycle" | Feed |
| PA | 59.3 | 9.33 | 13.6 |
| PAN | 23.8 | 51.2 | 48.9 |
| Benzoic Acid | 7.6 | 1.74 | 2.24 |
| o-Toluic Acid | 0.8 | 0 | 0.07 |
| Phthalide | 0.08 | 0.05 | 0.06 |
| High Boilers | 2.7 | 33.2 | 30.6 |
| o-Xylene | 0.13 | 0 | 0.01 |
| Carbon Oxides | 0.04 | 0 | 0.003 |
| Oxygen | 0.02 | 0 | 0.001 |
| Nitrogen | 0.04 | 0 | 0.004 |
| Co & Mn as Metals | 0.32 | 1.95 | 1.81 |
| Bromine | 0.38 | 2.35 | 2.18 |
| Water | 4.87 | 0 | 0.57 |

| Component | Film Evapoator | | | Crude PAN Product |
|---|---|---|---|---|
| | Feed | Vapor | Residue | |
| PA | 9.76 | 0 | 0 | 0 |
| PAN | 53.6 | 87.4 | 33.2 | 78.3 |
| Benzoic Acid | 1.87 | 2.8 | 0.42 | 7.9 |
| o-Toluic Acid | 0 | 0 | 0 | 0.83 |
| Phthalide | 0.08 | 0.08 | 0.02 | 0.09 |
| High Boilers | 22.6 | 0 | 51.5 | 0.32 |
| o-Xylene | 0 | 0 | 0 | 0.13 |
| Carbon Oxides | 0 | 0 | 0 | 0.04 |
| Oxygen | 0 | 0 | 0 | 0.02 |
| Nitrogen | 0 | 0 | 0 | 0.04 |
| Co & Mn as Metals | 3.06 | 0 | 6.98 | 0 |

TABLE V-continued

| FLUID STREAMS COMPONENTS, WEIGHT PERCENT | | | |
|---|---|---|---|
| Bromine | 3.44 | 0 | 7.85 | 0.02 |
| Water | 0.07 | 9.72 | 0 | 12.30 |

(b) Separation of Water Vapor from PAN

The 1182.3 kg/hr of 37 "Crude PAN Product" mixture of gases and vapors at a temperature of 227° C. and absolute pressure of 0.246 kg/cm² (0.24 atmosphere) flows through a condenser and is cooled to a temperature of from 132° to 135° C. At said temperature there condenses about 90% of the phthalic anhydride with a portion of each of benzoic acid, o-toluic acid, phthalide, higher boiling compounds and o-xylene if any be present. The condensate amounts to 903.35 kg/hr and is further processed in the next step. The uncondensed materials at 132°-135° C. comprising gases, the water vapor, the uncondensed PAN (10%), and the other aromatic derivatives present amounting to 278.94 kg/hr are fed to a tower having seven sieve trays and operated at a subatmospheric pressure of 0.13 atmosphere. The reflux liquid fed to the upper portion of said tower (i.e., above the top plate) is pseudocumene in an amount of 453.7 kg/hr and is at a temperature of 49° C. The gas-vapor mixture feed (278.94 kg/hr) enters the tower between the third and fourth trays from the bottom. The pseudocumene-water vapor mixture flows from the top of the tower to a condenser cooled to 49° C. The condensate collected forms a top pseudocumene layer which is recycled to the tower as reflux liquid and a bottom water layer 145.43 kg/hr which is drawn off and discarded. The materials flowing down the tower become enriched with respect to PAN as pseudocumene is vaporized therefrom by heat supplied by the tower's boiler. There is no significant concentration of pseudocumene in the liquid on the bottom tray at a temperature of 210° to 212° C. so that the liquid therefrom (mainly PAN with the parts of benzoic acid, o-toluic acid, and phthalide not first condensed at 132° to 135° C.) can be drawn off, about 128.5 kg/hr for further processing in the next step. Liquid flowing down from the first tray is heated in the boiler to a temperature of about 212° to 215° C. and recycled to the tower between the first and second trays.

(c) Removal of Phthalide

The 903.35 kg/hr of condensate at 132° to 135° C. and the 133.5 kg/hr of the 210° to 212° C. water and pseudocumene-free liquid bottoms from the water separation tower in step (b) are combined (combined liquids have a phthalide concentration of 0.103 weight percent) in a vessel operated at 0.24 atmosphere pressure and a temperature of 274° C. with 0.09 weight percent potassium hydroxide dissolved in water as a 50 weight percent KOH solution. The resulting mixture has a residence time of four hours at 274° C. temperature and subatmospheric pressure of 0.24 atmosphere.

(d) Fractionation

Liquid from the foregoing phthalide removal step is removed at 1032.78 kg/hr and fed to a first rectification tower operated at a top subatmospheric pressure of 0.16 atmosphere. A low boiling fraction at a temperature of 197° C. and a reflux ratio of 50:1 is removed at 113.3 kg/hr. Said low boiling fraction contains benzoic and o-toluic acids and PAN, the latter in a concentration of 8.9 weight percent. The liquid residue at a temperature of 222° C. from the first rectification tower is pumped at 919.28 kg/hr into a second rectification tower operated at a top subatmospheric pressure of 0.13 atmosphere. A PAN product fraction at 907.93 kg/hr is taken at a 2:1 reflux ratio and a temperature of 204.4° C. The liquid residue from this second rectification amounts to 11.35 kg/hr and contains 49 weight percent PAN.

The recovered PAN product has a purity of 99.9 weight percent, an initial color as a liquid of 5 to 10 on the APHA color (Pt-Co) scale and an aged liquid color (ASTM TEST D1209-69) of 20 on said APHA scale. The recovered PAN product amounts to 98 weight percent of the PAN charged to dehydration-evaporation step (a) and may contain 10 to 50 ppm bromine.

The invention claimed is:

1. A process for the formation, purification and recovery of phthalic anhydride from a mixture comprising on a weight basis from 70 up to 90 percent o-phthalic acid, from 1.5 up to 21 percent water, from 0.3 up to 13 percent benzoic acid, from 0.2 up to 2 percent o-toluic acid, from 0.1 up to 2 percent phthalide, from 0.2 up to one percent 2-carboxybenzaldehyde, and from 1.3 up to 4 percent higher boiling compounds; which process comprises subjecting said mixture as a liquid to the sequential steps of (a) rapid dehydration of o-phthalic acid to its anhydride under conditions for rapid evaporation of said anhydride wherein a mixture of vapors of said anhydride, water and the oxygen-containing aromatic compounds comprising benzoic acid, o-toluic acid, phthalide and 2-carboxybenzaldehyde is formed; (b) separating water vapor from said mixture of vapors by contacting in a fractionation zone such mixture of vapors in countercurrent flow with a reflux liquid at a temperature below the boiling temperature of said anhydride, which liquid is inert to the components of said mixture of vapors, a solvent for said anhydride at a temperature between its freezing point and its melting point, remains liquid at and below the freezing point temperature of said anhydride, boils at a temperature below the boiling point temperature of said anhydride, is substantially immiscible with water, and does not form an azeotrope with said anhydride; (c) removal of phthalide from the resulting water-free mixture of said anhydride and said oxygen-containing aromatic compounds by heating to a temperature above 250° C. such mixture of said anhydride and oxygen-containing aromatic compounds in the presence of an alkali metal hydroxide having a molecular weight of at least 56 until the presence of phthalide is no longer detectable; and (d) fractionation of the mixture resulting from step (c) to remove: as a first fraction substantially all of the benzoic acid, o-toluic acid and 2-carboxybenzaldehyde; as a second fraction product phthalic anhydride and leave as a third fraction the compounds boiling higher than phthalic anhydride.

2. The process of claim 1 wherein each of steps (a) through (d) is conducted continuously under a gauge pressure of from one atmosphere down to 0.05 atmosphere.

3. The process of claim 2 wherein the dehydration-evaporation of step (a) is conducted first to dehydrate 97 to 98 percent of o-phthalic acid to its anhydride, then to dehydrate the remainder of said acid to its anhydride with the injection of steam into the dehydrating mixture and the two vapor products therefrom are combined and fed to step (b).

4. The process of claim 3 wherein phthalic anhydride is condensed from the combined vapor mixtures at a temperature of 130° to 135° C. and the uncondensed vapors are contacted in step (b) with liquid pseudocumene as the reflux liquid in an amount of from 1.5 up to 3.0 moles per 1.0 mole of the total moles of materials in the uncondensed vapors.

5. The process of claim 3 wherein step (b) is conducted with methylbenzoate as the reflux liquid and in the liquid volume ratio of from 8:1 up to 20:1 of methylbenzoate to water.

6. The process according to claims 4 or 5 wherein step (c) is conducted with potassium hydroxide as the alkali metal in the amount of from 1.0 up to 10 milligram moles per 1.0 gram mole of impure phthalic anhydride and at a temperature of from 250° C. up to 350° C.

* * * * *

UNITED STATES PATENT AND TRADEMARK OFFICE
CERTIFICATE OF CORRECTION

PATENT NO. : 4,215,056
DATED : July 29, 1980
INVENTOR(S) : Hobe Schroeder et al.

It is certified that error appears in the above—identified patent and that said Letters Patent is hereby corrected as shown below:

Column 7, line 27, "refluxed" should read -- reflux --.

Column 14, line 9, "kg/hr of 37 "Crude PAN" should read -- kg/hr of "Crude PAN" --.

Column 16, line 37, "claims 4 or 5" should read -- claims 4 and 5 --.

Signed and Sealed this

Twelfth Day of May 1981

[SEAL]

Attest:

RENE D. TEGTMEYER

Attesting Officer

Acting Commissioner of Patents and Trademarks